(12) United States Patent
Siess et al.

(10) Patent No.: US 11,413,446 B2
(45) Date of Patent: Aug. 16, 2022

(54) BLOOD PUMP WITH REINFORCED CATHETER

(71) Applicant: ABIOMED EUROPE GMBH, Aachen (DE)

(72) Inventors: Thorsten Siess, Aachen (DE); Frank Kirchhoff, Aachen (DE)

(73) Assignee: ABIOMED EUROPE GMBH, Aachen (DE)

( * ) Notice: Subject to any disclaimer, the term of this patent is extended or adjusted under 35 U.S.C. 154(b) by 0 days.

(21) Appl. No.: 16/610,778

(22) PCT Filed: May 3, 2018

(86) PCT No.: PCT/EP2018/061356
§ 371 (c)(1),
(2) Date: Nov. 4, 2019

(87) PCT Pub. No.: WO2018/202779
PCT Pub. Date: Nov. 8, 2018

(65) Prior Publication Data
US 2020/0155739 A1    May 21, 2020

(30) Foreign Application Priority Data
May 4, 2017    (EP) .................................. 17169487

(51) Int. Cl.
*A61M 25/00*    (2006.01)
*A61K 9/22*    (2006.01)
(Continued)

(52) U.S. Cl.
CPC ........ *A61M 60/857* (2021.01); *A61M 25/005* (2013.01); *A61M 60/135* (2021.01); *A61M 2205/0266* (2013.01)

(58) Field of Classification Search
CPC ........ A61M 2205/0266; A61M 60/148; A61M 60/205; A61M 60/414; A61M 60/857; A61M 60/829
See application file for complete search history.

(56) References Cited

U.S. PATENT DOCUMENTS

| 5,108,411 A | 4/1992 | McKenzie | |
|---|---|---|---|
| 2008/0114339 A1* | 5/2008 | McBride | F04D 3/02 604/891.1 |

(Continued)

FOREIGN PATENT DOCUMENTS

| CN | 106512117 A | 3/2017 |
|---|---|---|
| EP | 0731720 B1 | 4/2002 |

(Continued)

OTHER PUBLICATIONS

International Search Report and Written Opinion for corresponding International Application No. PCT/EP2018/061356 dated Jun. 21, 2018 (9 pages).

(Continued)

*Primary Examiner* — Jon Eric C Morales
(74) *Attorney, Agent, or Firm* — Botos Churchill IP Law LLP

(57) ABSTRACT

An intravascular blood pump for percutaneous insertion comprises a catheter (10) and a pumping device (1) attached to the catheter (10). The catheter (10) extends along a longitudinal axis and has a distal end (11) and a proximal end (12) opposite the distal end (11). The catheter (10) comprises an elongate stiffening structure (15) extending continuously longitudinally along the length of the catheter (10) between the proximal end (11) and the distal end (12) of the catheter (10). The stiffening structure (15) may comprise a shape-memory material, such as Nitinol. It may be in the form of a wire that extends loosely through the (Continued)

lumen of the catheter and helps to avoid or significantly reduce kinks in the catheter.

20 Claims, 4 Drawing Sheets

(51) Int. Cl.
*A61M 60/857* (2021.01)
*A61M 60/135* (2021.01)

(56) References Cited

U.S. PATENT DOCUMENTS

| | | |
|---|---|---|
| 2013/0303969 A1 | 11/2013 | Keenan et al. |
| 2015/0141836 A1* | 5/2015 | Naumann ............ A61B 8/0833 600/463 |

FOREIGN PATENT DOCUMENTS

| | | |
|---|---|---|
| JP | H0724060 A | 1/1995 |
| WO | 9515192 A1 | 6/1995 |
| WO | 2007112033 A2 | 10/2007 |
| WO | 2011047884 A1 | 4/2011 |
| WO | 2013160443 A1 | 10/2013 |

OTHER PUBLICATIONS

Office Action for European Patent Application No. 18720634.7, dated Jan. 28, 2022, pp. 1-6.
Office Action issued in corresponding Indian Patent Application No. 201937041301 dated Feb. 1, 2022, (6 pp.).
Office Action issued in corresponding Japanese Patent Application No. 2019-560720 dated Mar. 15, 2022 (8 pp.).

* cited by examiner

BLOOD PUMP WITH REINFORCED CATHETER

CROSS-REFERENCE TO RELATED APPLICATIONS

This application is a United States National Stage filing under 35 U.S.C. § 371 of International Application No. PCT/EP2018/061356, filed May 3, 2018, which claims priority to European Patent Application No. 17169487.0, filed May 4, 2017. The contents of each of each of the foregoing applications are hereby incorporated by reference in their entirety. International Application No. PCT/EP2018/061356 was published under PCT Article 21(2) in English.

BACKGROUND

This invention relates to an intravascular blood pump for percutaneous insertion into a patient's blood vessel, comprising a catheter and a pumping device attached to the distal end of the catheter.

Blood pumps for percutaneous insertion are designed to support a patient's heart and are inserted into a patient's heart via a blood vessel such as the aorta or the femoral artery by means of a catheter through a vascular access in the patient's skin, i.e. percutaneously. An intravascular blood pump for percutaneous insertion typically comprises a catheter and a pumping device attached to the catheter. The catheter may extend along a longitudinal axis from a distal end to a proximal end, with the pumping device being attached to the catheter at the end remote from an operator, such as a surgeon. The pumping device may be inserted e.g. through the femoral artery and the aorta into the left ventricle of a patient's heart by means of the catheter. Blood pumps which are placed in a patient's heart may also be referred to as intracardiac blood pumps.

A relatively stiff catheter bears less risk of kinking, whereas a soft catheter better adapts to the shape of a blood vessel such as the aorta, in particular the aortic arch. However, soft catheters tend to kink in particular during insertion of the catheter because of their low rigidity. Once a catheter has kinked, this creates a weakened location on the catheter and it will most likely kink at the same location again. This may become particularly problematic during operation of the blood pump. For example, the blood pump may be pushed out of the heart back into the aorta, which may cause the catheter to kink, in particular if the catheter already kinked during insertion. This may result in a sharp kink at the weakened location, which in turn causes kinking of structures inside the catheter, such as a purge line that supplies purge fluid to the pumping device. The purge line can block and the blood pump can fail due to increased purge pressure or even complete blocking of the purge line.

SUMMARY OF THE INVENTION

It is therefore an object of the present invention to provide an intravascular blood pump for percutaneous insertion having a catheter which can be prevented from kinking.

This object is achieved according to the present invention by a blood pump for percutaneous insertion having the features of independent claim 1. Preferred embodiments and further developments of the invention are specified in the claims dependent thereon. Throughout this disclosure, the term "distal" will refer to directions away from a user and towards the heart, whereas the term "proximal" will refer to directions towards a user.

According to the invention, the catheter of an intravascular blood pump for percutaneous insertion comprises an elongate stiffening structure that extends continuously longitudinally along the length of the catheter between the proximal end and the distal end of the catheter. The stiffening structure has a minimum bending stiffness of about 0.00005 $Nm^2$ to about 0.01 $Nm^2$, preferably about 0.0001 $Nm^2$ to about 0.001 $Nm^2$, more preferably about 0.0001 $Nm^2$ to about 0.0005 $Nm^2$, more preferably about 0.0001 $Nm^2$ to about 0.0007 $Nm^2$ or about 0.00005 $Nm^2$ to about 0.0004 $Nm^2$, and is not subject to plastic deformation if bent with a minimum bending radius 10 mm. The catheter is, thus, reinforced by means of the elongate stiffening structure and prevented from kinking.

In one embodiment, the stiffening structure comprises a shape-memory material. The continuous stiffening structure of a shape-memory material prevents the catheter from kinking while at the same time providing sufficient flexibility to enable bending so that the catheter can be directed through a blood vessel, such as the aorta. This is particularly caused by so-called superelastic properties of the material. Shape memory materials have temperature dependent properties and temperature independent properties. Shape memory is a temperature dependent property that allows the shape memory material the ability to undergo deformation at one temperature and then recover its original, undeformed shape upon heating above its "transformation temperature". The temperature change causes a transformation between the martensite phase and austenite phase of the material. Superelasticity is a temperature independent property that allows the shape memory material the ability to undergo a mechanical deformation due to an external force applied to the shape memory material, and then recover its original undeformed shape upon release of the external force. The superelasticity, which is also referred to as pseudoelasticity, is caused by a transformation between the martensite phase and the austenite phase that occurs due to external loads. As a result, these materials can reversibly deform to very high strains. A preferred shape-memory material is Nitinol.

Kinks are prevented particularly during percutaneous insertion of the blood pump whereby a surgeon/cardiologist pushes the catheter through the blood vessel. Weakened locations on the catheter are avoided such that there is less risk of the catheter kinking during operation of the blood pump. Should a catheter kink during the procedure nevertheless, then it will have a chance to flex back and the catheter can recover its shape over time. In particular, since a kink is a plastic deformation of the catheter, i.e. a nonreversible deformation, whereas bending is an elastic deformation where the catheter can return to its initial shape, the stiffening structure allows the catheter to be elastically deformed with a minimum bending radius of 10 mm without the occurrence of plastic deformation. The bending radius is measured with respect to a central axis of the catheter. In combination with the bending stiffness of about 0.00005 $Nm^2$ to about 0.01 $Nm^2$, the stiffening structure provides effective avoidance of kinks or at least significant reduction of kinks.

The bending stiffness (or flexural rigidity) is a mechanical value of the stiffening structure, depending on the material and dimensions, more specifically a product of the modulus of elasticity ("Young's modulus") and the moment of inertia, which in turn depends on the cross-sectional area (size and shape). A typical diameter for a stiffening wire is for instance between 0.5 mm and 0.6 mm. Assuming a wire with a circular cross sectional shape this results in a moment of inertia of about 0.0031 $mm^4$ to about 0.0064 $mm^4$. Exemplary values for the modulus of elasticity may be about 70-90 GPa for austenitic Nitinol and about 20-45 GPa for martensitic Nitinol. This results in a bending stiffness of about 0.0002 Nm$^2$ to about 0.0006 Nm$^2$ for austenitic Nitinol and about 0.00006 Nm$^2$ to about 0.0003 Nm$^2$ for martensitic Nitinol.

In a preferred embodiment the stiffening structure is a wire with a cross-sectional shape having a diameter between 0.54 mm and 0.56 mm and the material thereof having a modulus of elasticity between 73 and 85 GPa for austenitic Nitinol and between 23 and 42 GPa for martensitic Nitinol.

The stiffening structure may extend along the length of the catheter at least in a region where high bending forces may occur, such as the distal end of the catheter, e.g. at least 20 cm, preferably at least 30 cm from the distal end. Preferably, the stiffening structure extends along the region of the catheter that is placed inside the patient's body, such as at least 40 cm from the distal end of the catheter. More preferably, the stiffening structure extends further in a region of the catheter which will be handled by a surgeon, i.e. at least 50 cm from the distal end of the catheter. Most preferably, the stiffening structure extends along the entire length of the catheter. A typical length of a catheter for percutaneous insertion via a femoral access (arterial or venous) into the patient's heart can be between 100 to 150 cm. The stiffening structure can also have a length between 100 and 150 cm. The catheter and stiffening structure may have a length between 25 and 50 cm in case the catheter is designed for insertion through the subclavian or axillary artery into the left ventricle or through the jugular vein into the right ventricle.

The stiffening structure may be configured to stay in the catheter during operation of the blood pump in order to support the catheter and prevent kinks during the entire surgical procedure and during operation of the blood pump. This may be advantageous in applications in which the blood pump tends to be pushed out of the heart during operation of the blood pump, either by movements of the heart or by the pumping action of the blood pump. In applications in which there is no or less tendency of pushing the blood pump out of the heart the stiffening structure may be configured to be removed from the catheter after placement of the blood pump in the patient's body. This renders the catheter more flexible during operation of the blood pump and allows the catheter to better adapt to the shape of the respective vessel, such as the aorta. This reduces contact between the inner wall of the vessel and the catheter and may also reduce the force with which the pump may push against a valve structure.

As mentioned above, the stiffening structure preferably comprises or is made of a material with superelastic characteristics, in particular a shape-memory material, i.e. a material that has the ability to return to its original shape after it has been deformed and that resists permanent kinks. The shape-memory material may be a shape-memory alloy, preferably Nitinol. In particular Nitinol exhibits superelastic characteristics, which aid in preventing kinks. However, other shape-memory materials, such as a polymeric material having shape-memory properties may be used for the stiffening structure. Also carbon fiber reinforced materials can be used.

The use of a Nitinol structure outside a catheter is described in WO 2013/160443 A1. An optical fiber extends through the catheter and exits the catheter to extend further along the outside of a cannula within a Nitinol tube. The optical fiber is placed inside the catheter without the Nitinol tube. In contrast to this, the present invention provides a stiffening structure made of a shape-memory material, such as a Nitinol rod or wire or tube, that extends continuously along the length of the catheter to avoid kinking of the catheter. The stiffening structure may be provided for stiffening purposes only. In particular, the stiffening structure is preferably separate from, i.e. not connected to the pumping device. In some embodiments, however, the stiffening structure may have an additional function, such as a guiding or protecting function.

The catheter may have a lumen, such as at least one lumen, that extends through the catheter from the proximal end to the distal end. The stiffening structure is preferably disposed inside the lumen of the catheter. If the catheter has more than one lumen, the stiffening structure may be disposed in a lumen separate from a lumen that contains other lines, e.g. electric lines, purge lines etc. Thus, a common catheter can be used and provided with the stiffening structure by insertion of the stiffening structure through the catheter lumen. Preferably, the stiffening structure is substantially free-floating or loose, i.e. not fixed, inside the lumen of the catheter. Particularly the distal end of the stiffening structure may be free, i.e. not attached to or operatively connected to other parts of the blood pump, e.g. the pumping device. This enhances flexibility of the catheter while at the same time effectively preventing the catheter from kinking because the stiffening structure may move and slide inside the catheter lumen when the catheter is bent to follow a shape of a blood vessel. This has the further effect that the flexibility of the catheter may have an isotropic behavior, i.e. the flexibility may be identical in any bending direction, because the stiffening structure is not fixedly attached to one side of the catheter.

Alternatively, the stiffening structure may be contained or embedded in a wall of the catheter or placed on an outer surface of the catheter rather than being inserted into the lumen of the catheter. The stiffening structure may be fixed at least in a radial direction. It may be movable in an axial direction to be able to slide in the axial direction along the length of the catheter e.g. when the catheter is bent. For instance, the stiffening structure may be secured on the outer surface of the catheter by means of any suitable attachments, like rings, loops, eyelets or the like. Alternatively, the stiffening structure may be fixed on the outer surface of the catheter along its entire length.

In one embodiment, the stiffening structure comprises at least one rod or wire. In another embodiment, the stiffening structure comprises a plurality of rods or wires, such as two, three, four or more rods or wires. It will be appreciated that the properties with respect to bending stiffness of the one or more rods or wires add up to provide a desired overall bending stiffness.

Preferably, the at least one rod or wire is solid, with preferably each of the rods or wires being solid. A solid rod is an easy-to-manufacture and cheap construction for providing the stiffening structure. In another embodiment, the rod may have a hollow cross-section, i.e. it may be tubular. In case of a tubular rod or wire, this tube can be used for example to supply a purge fluid to a blood pump. The at least one rod, preferably each of the rods, may have a diameter of about 0.3 to 0.6 mm, preferably about 0.54 to 0.56 mm. The diameter of the rod or rods does not have to be constant along the length, but may be variable to achieve a variable flexibility along the length. For example, in regions where the catheter is to be stiffer, the rod or rods may have a larger diameter than in regions where the catheter is to be softer or by having a multitude of rods acting simultaneously in said regions. A variable flexibility can also be created by providing different materials along the length of the rod or by providing a jacket to provide increased bending stiffness in desired regions. Preferably, the stiffening structure provides a greater stiffness at its proximal end, i.e. the end which is operated by a user and, thus, may need a higher bending stiffness. The distal end may have a lower bending stiffness than the proximal end to allow the catheter to be advanced into the blood vessel. For this purpose, the stiffening structure may be tapered towards the distal end.

The rod or rods may have any appropriate cross-sectional shape, particularly circular or other shapes, such as oval or polygonal, in particular triangular, rectangular, pentagonal, hexagonal or octagonal. It will be appreciated that one relatively thick rod may achieve the same, or roughly the same, effect as a plurality of thinner rods, such as two, three, four or more. If the stiffening structure comprise more than one rod, the rods may be braided, either forming a substantially solid braid or a braided tube, i.e. a hollow tubular body. Depending on the number of rods, e.g. if three rods are braided, a solid braid may have different bending stiffnesses in different directions, whereas a braided tube may provide the same bending stiffness in every direction and may provide a high torsional stiffness.

In one embodiment, the stiffening structure may have a cross-section which is not rotationally symmetric. In particular, the cross-section may have at least two, in particular two, intersecting axes of symmetry, preferably perpendicular axes of symmetry. Such cross-section may be e.g. oval or rectangular. This kind of symmetry may also be achieved by placing more than one rod adjacent two each other, e.g. two rods with a circular cross-section. More generally, the bending stiffness of the stiffening structure may vary with respect to bending of the stiffening structure in different planes. This may be useful in navigation of the catheter. In particular, the catheter may be curved in a plane and the stiffening structure may have a minimum bending stiffness with respect to bending in said plane in which the catheter is curved. That means that the catheter can be bent more easily in the plane in which it is curved while lateral bending in other planes is more difficult.

Preferably, the at least one rod or wire is straight or linear, which means that it does not have any undulations or the like except for the curvature that results from the curvature of the catheter.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings.

DETAILED DESCRIPTION

Figure 1:
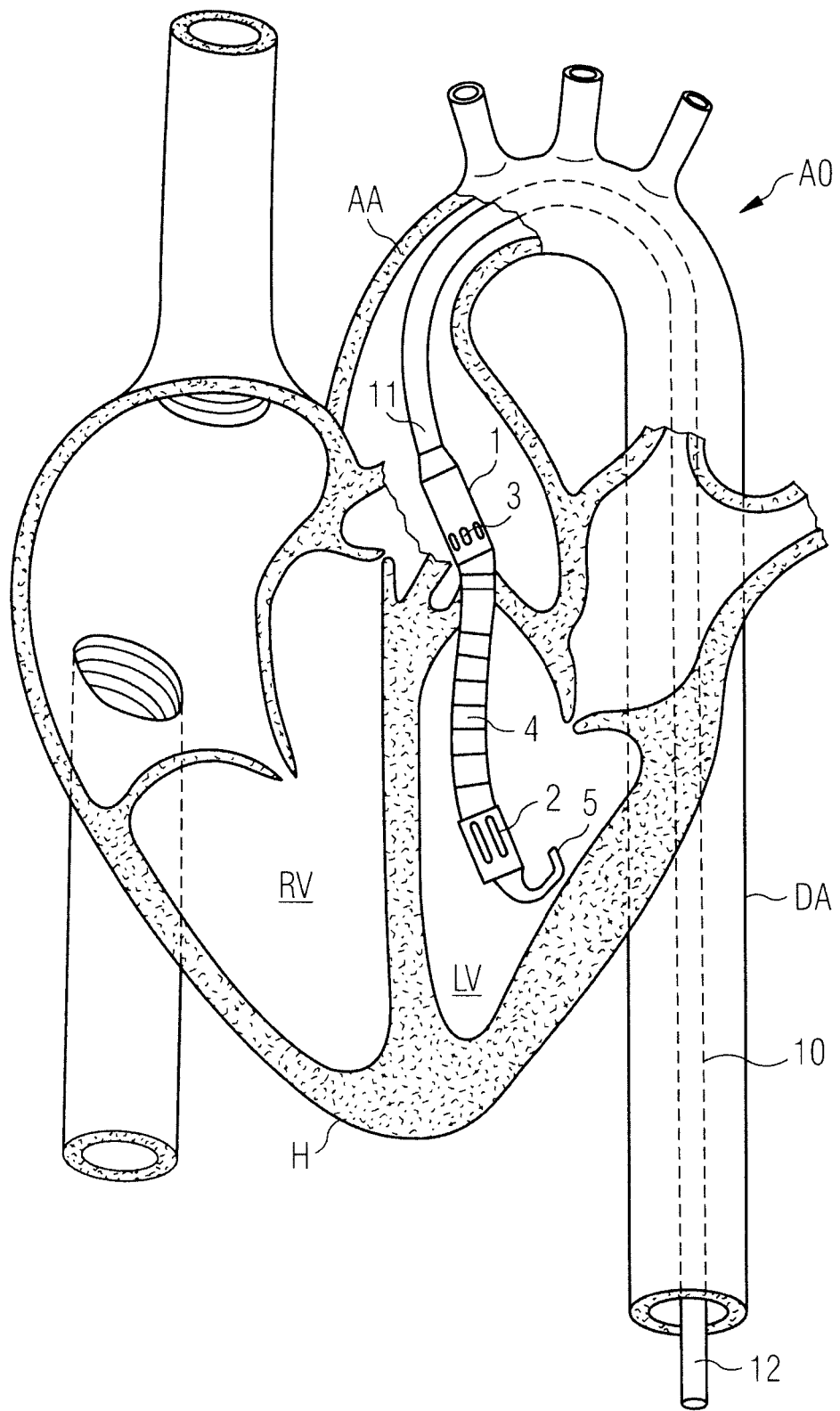
FIG. 1 shows a patient's heart with a blood pump inserted through the aorta into the left ventricle.

In FIG. 1 is illustrated a blood pump inserted into a patient's heart H. More specifically, the blood pump comprises a pumping device 1 attached to a catheter 10 by means of which the pumping device 1 is inserted into the left ventricle LV of the patient's heart H via the aorta AO, including the descending aorta DA and the aortic arch AA. The catheter 10 has a distal end 11 and a proximal end 12. The blood pump has a blood flow outlet 3 that is disposed outside the patient's heart H in the aorta AO, while a blood flow inlet 2 is in flow communication with a flow cannula 4 placed inside the left ventricle LV. An impeller (not shown) is provided in the pumping device 1 to cause the blood flow from the blood flow inlet 2 to the blood flow outlet 3. At the distal end of the blood pump, a soft tip 5, such as a pigtail or J-tip, is arranged to facilitate insertion of the blood pump into the patient's heart H without causing any harm to the surrounding tissue. Also, the soft tip 5 helps to keep soft tissue away from the blood flow inlet 2 and to support the pumping device 1 against the inner wall of the left ventricle LV.

Figure 2:
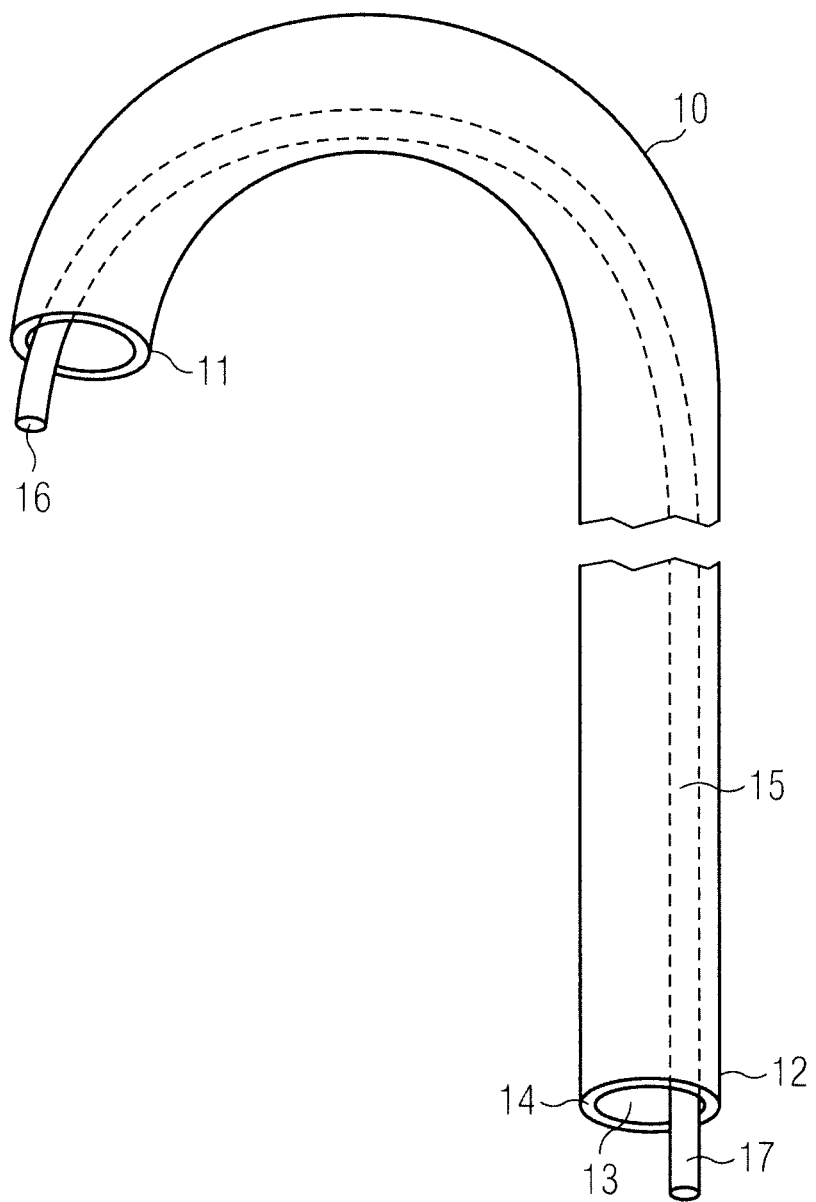
FIG. 2 schematically shows the catheter of the blood pump of FIG. 1 with a stiffening structure.

Referring now to FIG. 2, the catheter 10 of the blood pump of FIG. 1 is shown. The catheter 10 extends from the distal end 12 to the proximal end 11 and has a lumen 13 that extends through the catheter 10. The pumping device 1 which is attached to the distal end 11 of the catheter 10 as shown in FIG. 1 is not shown in FIG. 2. The lumen 13 of the catheter 10 is defined by a wall 14 of the catheter 10, which may have a wall thickness of about 0.1 to 1 mm, such as 0.5 mm. The catheter 10 may have an outer diameter of 2 mm to 4 mm, such as about 3 mm (corresponding to a dimension of 9 French). Accordingly, the inner diameter of the catheter may be for instance about 2 mm (corresponding to a dimension of 7 French). A stiffening structure in the form of an elongated rod 15 is disposed inside the catheter lumen 13 and extends from a distal end 16 to a proximal end 17. It extends continuously through the catheter 10 from the catheter's distal end 11 to its proximal end 12. Other structures that may extend through the catheter 10, such as a purge line or electric wire, are omitted in FIG. 2 for the sake of clarity.

The rod 15 is particularly made of Nitinol and provides a bending stiffness sufficient to prevent the catheter 10 from kinking, while permitting the catheter 10 to bend to adapt to the shape of the blood vessel, such as the aorta AO, in particular the aortic arch AA. As illustrated in FIG. 2, the rod 15 is free-floating in the lumen 13 of the catheter 10, i.e. loose and not fixed inside the catheter 10. Thus, it may follow a slightly different radius of curvature than the catheter 10 while moving inside the catheter lumen 13. The rod 15 is also permitted to slide inside the lumen 13, in particular axially, which may be advantageous for the flexibility of the catheter 10. The distal end 16 of the rod 15 is free, in particular not attached to the pumping device 1 or parts of the pumping device 1. Both, distal and proximal, ends of the rod 15 or at least one end thereof may be protected or encapsulated with a soft tip to avoid penetration into the catheter 10 or other adjacent structures.

The rod-like stiffening structure preferably has a solid cross-section, i.e. no lumen or the like extending therethrough, and may have different cross-sectional shapes.

In another embodiment (not shown), the rod may be tubular and may act as a line for a purge fluid or for supplying a gas. The tubular rod may, therefore, be attached to the pump or other structure that requires the presence of transported fluid or gas.

Figure 3:
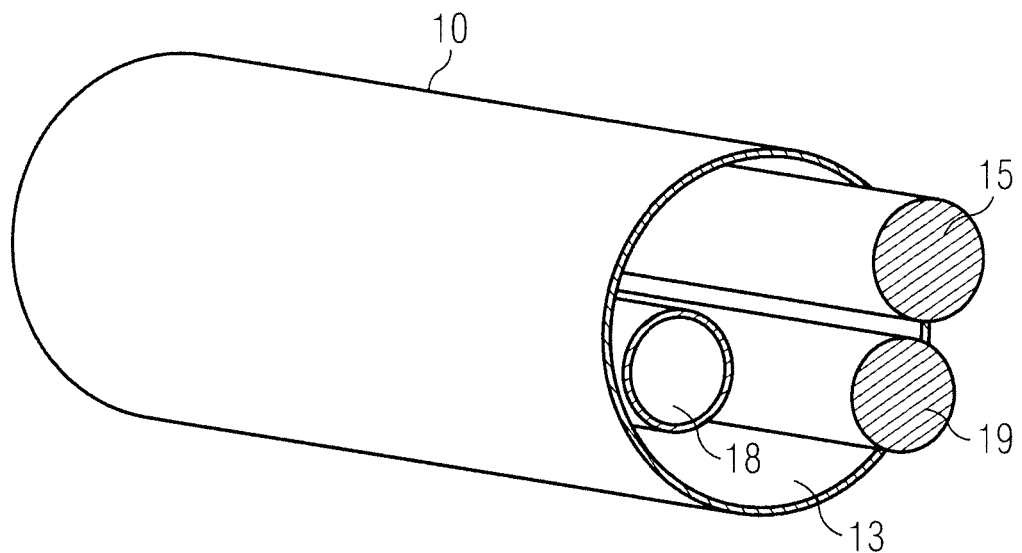
FIGS. 3 to 5 schematically show the catheter with a stiffening structure in accordance with different embodiments.
Figure 4:
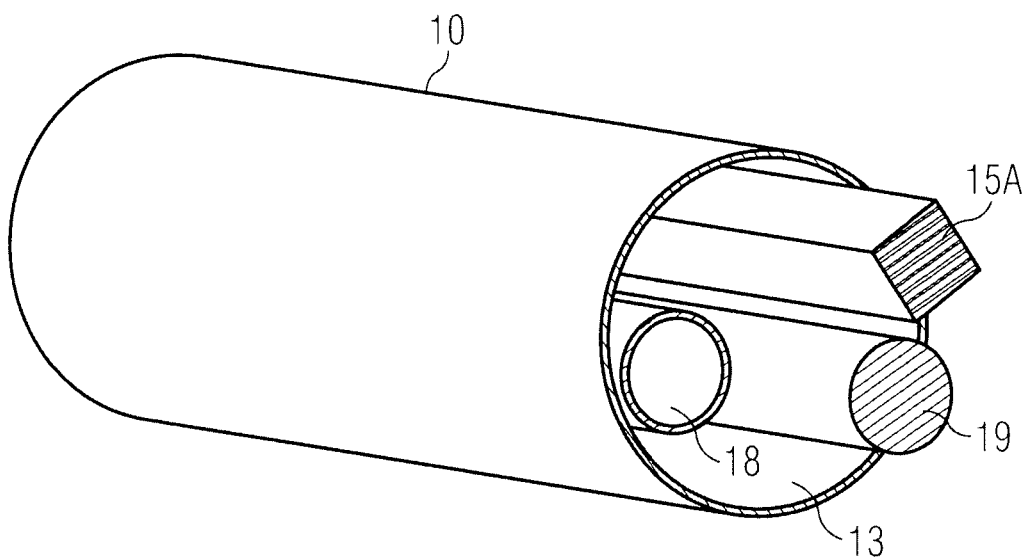
Figure 5:
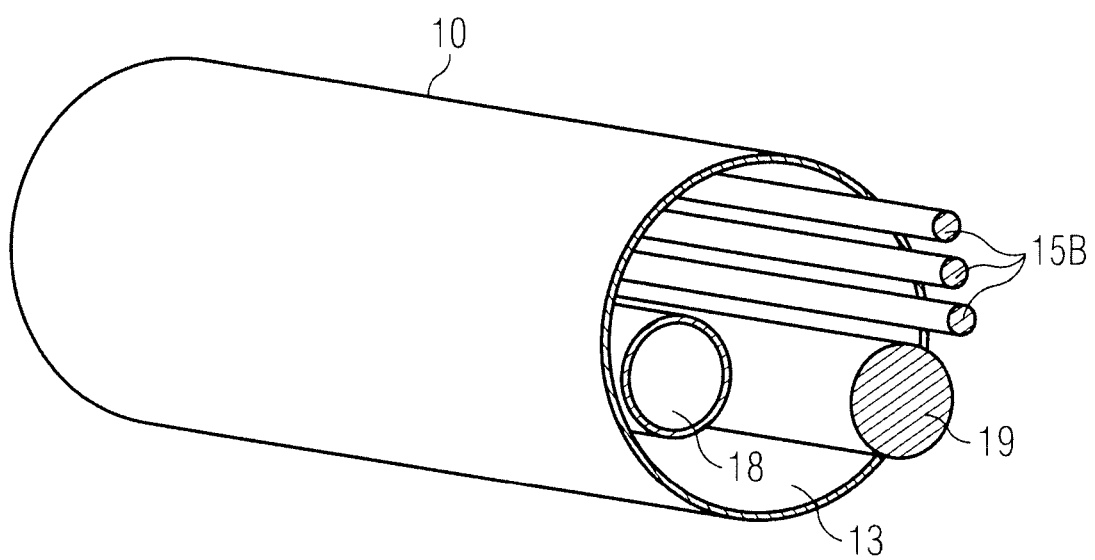

The cross-sectional shape is preferably circular or substantially circular as shown in FIG. 3. In another embodiment, the rod 15A may have a rectangular or square cross-section as illustrated in FIG. 4. In still another embodiment, a plurality of rods 15B may be provided, such as three rods 15B as shown in FIG. 5. Said rods 15B may be identically formed with respect to shape and size or may be different. In another embodiment (not shown) the multiple rods may be braided. The bending stiffnesses of the rods 15B add up to the desired total bending stiffness of the stiffening structure.

It will be appreciated that any of the stiffening structures 15, 15A and 15B may be combined with each other. As shown in FIGS. 3 to 5, a purge fluid line 18 for supplying a purge fluid to the pumping device 1, and an electric wire 19 for supplying electric power to the pumping device 1, may be inserted in the catheter lumen 13. The stiffening structure 15 is particularly useful for preventing the catheter 10 from kinking, which would occlude the purge line 18 and lead to failure of the blood pump because the purge pressure is too high or lubricating is interrupted.

As described above a rod 15 may extend longitudinally through the catheter 10 in a straight manner to increase the catheter's resistance to kinking. The rod 15 may be inserted in the catheter 10 during insertion of the pumping device 1 into the patient. The rod 15 may stay in the catheter or may be removed to render the catheter 10 flexible after insertion, therefore less traumatic to surrounding tissue.

Regardless of its shape, size and configuration, the stiffening structure 15 comprises or is made of a shape-memory material, preferably a shape-memory alloy, in particular Nitinol. Not least because of this material the stiffening structure 15 allows the catheter 10 to be bent, i.e. elastically deformed, with a bending radius of 10 mm or less without kinking, i.e. without the occurrence of plastic deformation. The bending radius is measured with respect to a central axis of the catheter. Thus, the catheter 10 with the stiffening structure 15 made of a shape-memory material, e.g. a catheter with a Nitinol wire, provides a better bending stiffness. The desired bending stiffness characteristics result mainly from the superelastic properties of the Nitinol. Preventing kinking of the catheter is important, for instance to avoid occlusion of tubular lines inside the catheter.

The invention claimed is:

1. An intravascular blood pump for percutaneous insertion into a patient's blood vessel, comprising:
    a catheter, and
    a pumping device attached to the catheter, the catheter extending along a longitudinal axis and having a distal end and a proximal end opposite the distal end along the longitudinal axis, the catheter comprising an elongate stiffening structure extending continuously longitudinally along a length of the catheter between the proximal end and the distal end of the catheter,
    wherein the stiffening structure comprises at least one rod or wire having a cross-section that is not rotationally symmetric, and
    wherein the stiffening structure has a minimum bending stiffness of about 0.00005 $Nm^2$ to about 0.01 $Nm^2$ and is not subject to plastic deformation if bent with a minimum bending radius 10 mm.

2. The blood pump of claim 1, wherein the catheter has at least one lumen that extends through the catheter from the proximal end to the distal end, with the stiffening structure being disposed in the lumen of the catheter.

3. The blood pump of claim 2, wherein the stiffening structure is loose inside the lumen of the catheter.

4. The blood pump of claim 1, wherein the stiffening structure comprises a plurality of rods or wires.

5. The blood pump of claim 1, wherein the at least one rod or wire is solid.

6. The blood pump of claim 1, wherein the at least one rod or wire is straight.

7. The blood pump of claim 4, wherein the plurality of rods or wires are braided.

8. The blood pump of claim 1, wherein the stiffening structure comprises a shape-memory material.

9. The blood pump of claim 8, wherein the shape-memory material is Nitinol.

10. The blood pump of claim 1, wherein the stiffening structure is configured to stay in the catheter during operation of the blood pump.

11. The blood pump of claim 1, wherein the stiffening structure is configured to be removed from the catheter after placement of the blood pump in a patient's body.

12. The blood pump of claim 1, wherein the cross-section of the at least one rod or wire has at least two intersecting axes of symmetry.

13. An intravascular blood pump for percutaneous insertion into a patient's blood vessel, comprising:
    a catheter, and
    a pumping device attached to the catheter, the catheter extending along a longitudinal axis and having a distal end and a proximal end opposite the distal end along the longitudinal axis, the catheter comprising an elongate stiffening structure extending continuously longitudinally along a length of the catheter between the proximal end and the distal end of the catheter,
    wherein the stiffening structure has a minimum bending stiffness of about 0.00005 $Nm^2$ to about 0.01 $Nm^2$ and is not subject to plastic deformation if bent with a minimum bending radius 10 mm, and
    wherein a bending stiffness of the stiffening structure varies with respect to bending of the stiffening structure in different planes.

14. The blood pump of claim 13, wherein the catheter is curved in a plane and wherein the stiffening structure has a minimum bending stiffness with respect to bending in said plane in which the catheter is curved.

15. The blood pump of claim 13, wherein the catheter has at least one lumen that extends through the catheter from the proximal end to the distal end, with the stiffening structure being disposed in the lumen of the catheter.

16. The blood pump of claim 15, wherein the stiffening structure is loose inside the lumen of the catheter.

17. The blood pump of claim 13, wherein the stiffening structure comprises a shape-memory material.

18. The blood pump of claim 17, wherein the shape-memory material is Nitinol.

19. The blood pump of claim 13, wherein the stiffening structure is configured to stay in the catheter during operation of the blood pump.

20. The blood pump of claim 13, wherein the stiffening structure is configured to be removed from the catheter after placement of the blood pump in a patient's body.

* * * * *